United States Patent
Carlyon et al.

(10) Patent No.: US 7,833,201 B2
(45) Date of Patent: Nov. 16, 2010

(54) FLASHBACK CHAMBER VISUAL ENHANCEMENT

(75) Inventors: James L. Carlyon, Farmington, MO (US); Eugene F. Schrader, St. Louis, MO (US); Richard L. Fiser, Wildwood, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 75 days.

(21) Appl. No.: 11/904,466

(22) Filed: Sep. 27, 2007

(65) Prior Publication Data

US 2008/0082053 A1    Apr. 3, 2008

Related U.S. Application Data

(60) Provisional application No. 60/848,250, filed on Sep. 29, 2006.

(51) Int. Cl.
*A61M 5/178* (2006.01)

(52) U.S. Cl. .................. 604/168.01; 604/276

(58) Field of Classification Search ............ 604/168.01; 600/407; 128/214
See application file for complete search history.

(56) References Cited

U.S. PATENT DOCUMENTS

| | | | |
|---|---|---|---|
| 3,500,828 A | 3/1970 | Podhora | |
| 4,317,445 A | 3/1982 | Robinson | |
| 4,365,630 A * | 12/1982 | McFarlane | 604/168.01 |
| 4,610,671 A | 9/1986 | Luther | |
| 4,767,408 A * | 8/1988 | McFarlane | 604/168.01 |
| 4,777,953 A | 10/1988 | Ash et al. | |
| 4,832,034 A | 5/1989 | Pizziconi et al. | |
| 4,908,021 A * | 3/1990 | McFarlane | 604/168.01 |
| 4,959,196 A | 9/1990 | Moisson | |
| 4,961,729 A | 10/1990 | Vaillancourt | |
| 4,989,606 A | 2/1991 | Gehrich et al. | |
| 5,029,583 A | 7/1991 | Meserol et al. | |
| 5,279,572 A | 1/1994 | Hokama | |
| 5,368,029 A | 11/1994 | Holcombe et al. | |
| 5,755,709 A | 5/1998 | Cuppy | |
| 5,820,570 A | 10/1998 | Erickson et al. | |
| 6,440,119 B1 | 8/2002 | Nakada et al. | |
| 6,524,277 B1 | 2/2003 | Chang | |
| 6,991,898 B2 | 1/2006 | O'Connor | |
| 7,025,746 B2 | 4/2006 | Tal | |
| 7,225,689 B2 | 6/2007 | Wickstead et al. | |
| 7,276,027 B2 | 10/2007 | Haar et al. | |

(Continued)

OTHER PUBLICATIONS

International Search Report from co-pending International Appln. No. PCT/US07/020997 mailed Apr. 1, 2008.

*Primary Examiner*—Nicholas D Lucchesi
*Assistant Examiner*—Gerald Landry, II
(74) *Attorney, Agent, or Firm*—Lisa E. Winsor, Esq.

(57) ABSTRACT

Featured is a medical infusion device for vascular access with enhanced flashback visualization that includes a hub assembly having a flashback chamber. The hub assembly includes a proximal portion, a distal portion and a substantially transparent window section intermediate the proximal portion and distal portion. A needle is coupled to the flashback chamber so that fluid flows through the lumen of the needle into the flashback chamber after the needle is inserted into a blood vessel. A contrasting member is disposed on at least a portion of the hub assembly, so that when blood enters the flashback chamber, the contrasting member provides a high-contrast background when viewed through the window section.

19 Claims, 14 Drawing Sheets

U.S. PATENT DOCUMENTS

| | | | |
|---|---|---|---|
| 2002/0004647 A1* | 1/2002 | Leong | 604/168.01 |
| 2002/0055715 A1* | 5/2002 | Young et al. | 604/164.04 |
| 2002/0115922 A1* | 8/2002 | Waner et al. | 600/407 |
| 2002/0115964 A1 | 8/2002 | Boudreaux | |
| 2004/0106903 A1* | 6/2004 | Shue et al. | 604/168.01 |
| 2004/0111059 A1* | 6/2004 | Howlett et al. | 604/164.13 |
| 2004/0204685 A1* | 10/2004 | Wright et al. | 604/174 |
| 2005/0084842 A1 | 4/2005 | O'Connor | |
| 2007/0287989 A1 | 12/2007 | Crawford et al. | |

* cited by examiner

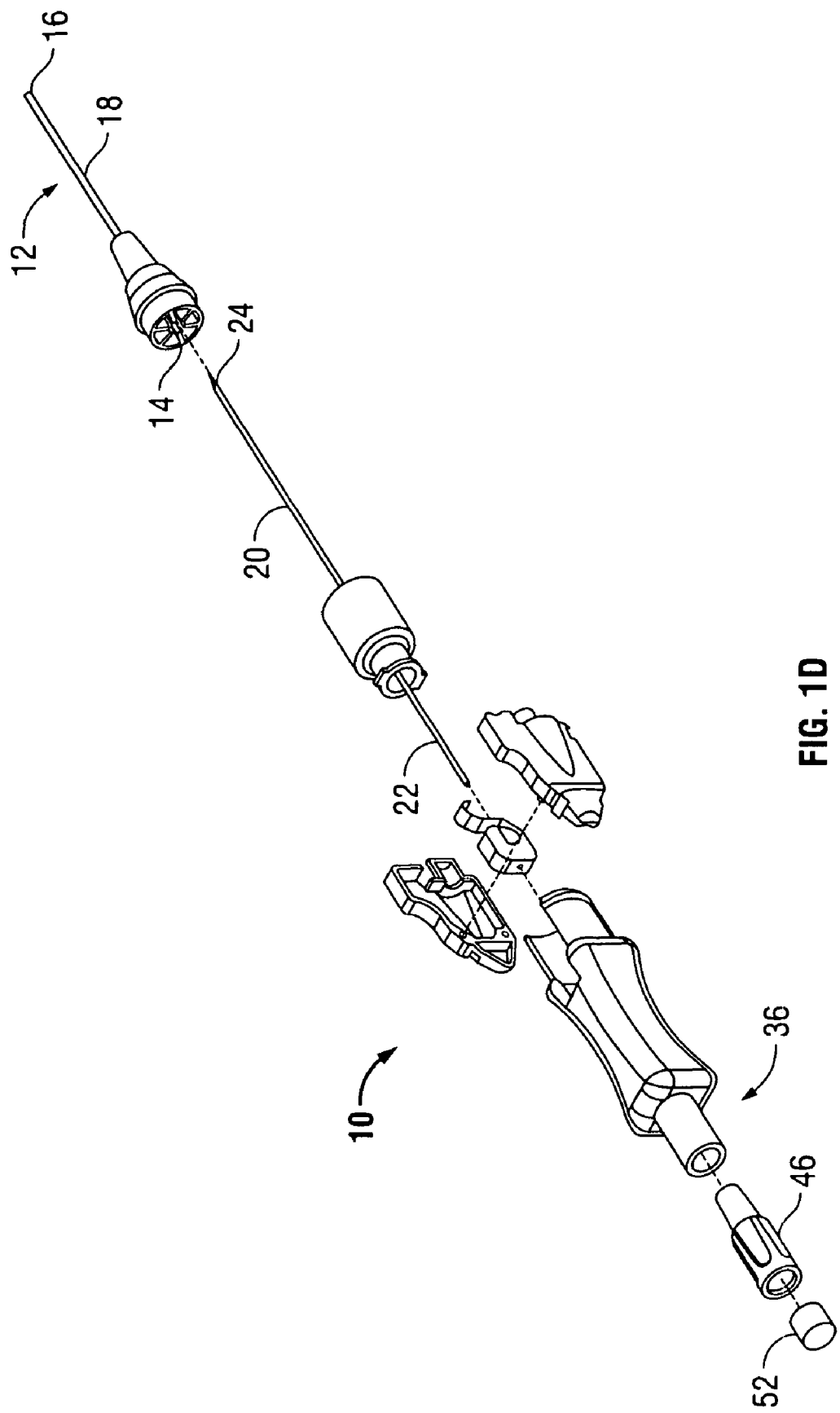

FIG. 3E     FIG. 3F

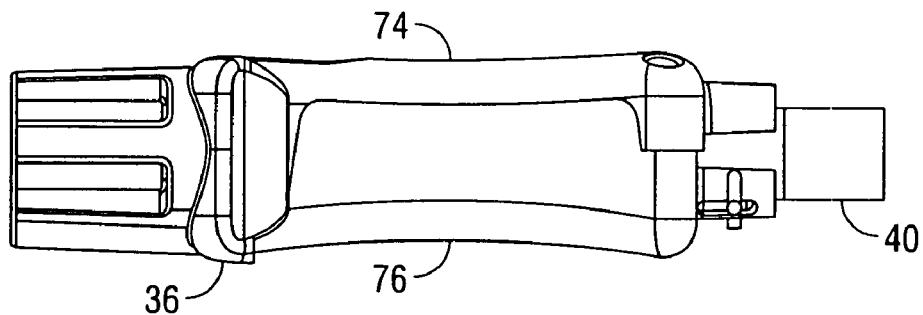
FIG. 3M
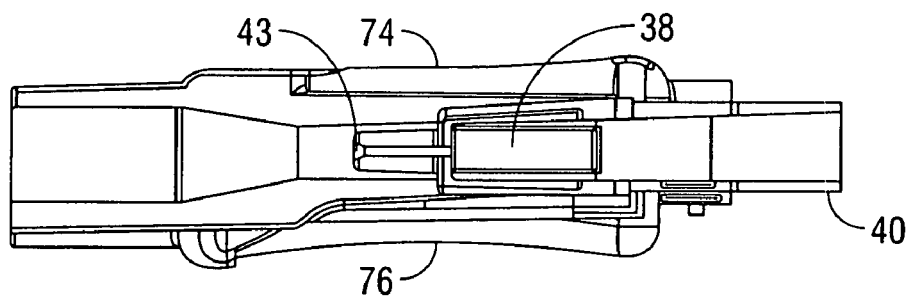
FIG. 3N
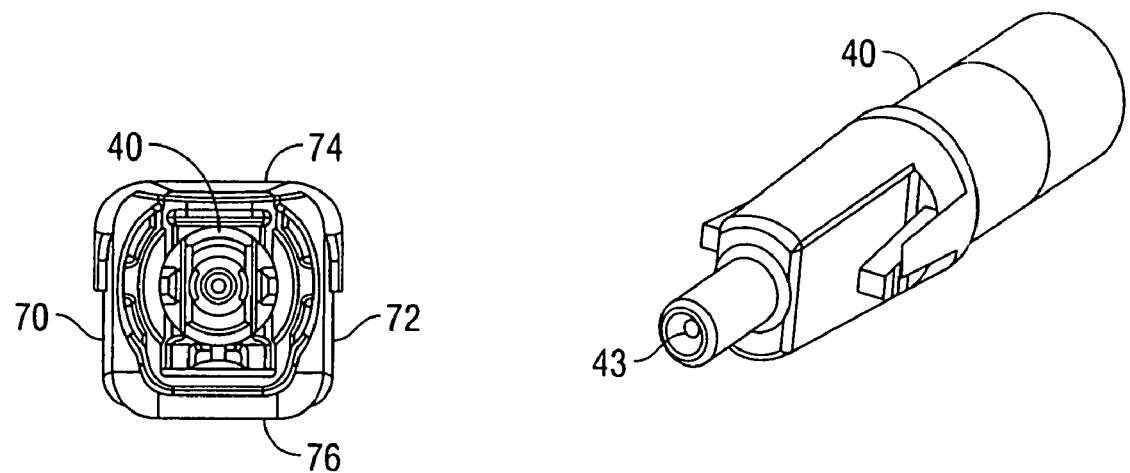
FIG. 3O
FIG. 3P

FLASHBACK CHAMBER VISUAL ENHANCEMENT

This application claims priority from U.S. Provisional Application Ser. No. 60/848,250 filed Sep. 29, 2006, the entire contents of which is incorporated herein by reference.

FIELD OF DISCLOSURE

The present disclosure relates to medical infusion or access devices such as intravenous (IV) catheters and more particularly to a vascular access device including a chamber for increased visualization of fluid when an intravenous catheter is inserted into the vasculature or blood vessel of the patient.

BACKGROUND INFORMATION

Over-the-needle catheters or over-the-needle IV catheters (such as that described in U.S. Patent Publication No. 2005-0096592, filed Oct. 31, 2003 to Carlyon et al.) are used for peripheral intravenous entry into the vasculature of a patient. The disposable medical product is packaged as an assembly of a catheter adapter with its catheter, and a needle/hub assembly that is arranged with respect to the catheter adapter so the needle passes through the catheter tube. The needle also extends a slight distance beyond the distal tip of the catheter tube so as to provide a sharpened point for penetration through the skin of the human or animal being catheterized.

After the catheter adapter with its catheter, and a needle/hub assembly are inserted into the vasculature or blood vessel of the patient, blood flows due to the vascular blood pressure through the hollow needle and into the needle hub, sometimes referred to as flashback. Typically, the needle hub is arranged and configured so the medical personnel are provided a visual indicator of the blood flashback. This visual indicator is used to indicate that the tip of the needle and thus the distal end of the catheter tube is disposed in the blood vessel. In one technique, the needle hub includes a chamber that is fluidly coupled to the needle and is made at least in part of a transparent material so that the blood flashback into the chamber is visually apparent to the medical personnel.

Even though such chambers are transparent, blood in the flashback chamber of these devices can sometimes be difficult to visualize in certain situations such as low light conditions or against darker backgrounds. It thus would be desirable to provide a new vascular access device such as an IV catheter device with enhanced flashback visualization. It would be particularly desirable to provide such a device that provides a high-contrast background to maximize flashback visibility. It would be further desirable to provide a device that facilitates earlier detection of blood or other fluids in the flashback chamber with greatly improved flashback visibility when used in low light situations or on patients with dark complexions. It also would be desirable to provide such a device that is less complex in stricture, manufacture and operation as compared to prior art devices. Also it would be desirable that such methods would not require users to have higher skills than those who ordinarily use such catheter devices.

SUMMARY OF THE INVENTION

The present invention is a medical infusion device for vascular access with enhanced flashback visualization. In one embodiment, the device includes a hub assembly having a flashback chamber. The hub assembly has a proximal portion, a distal portion and a substantially transparent window section disposed between the proximal portion and distal portion. A needle that includes a lumen is coupled to the flashback chamber so that fluid, such as blood, flows through the lumen of the needle into the flashback chamber after the needle is inserted into a blood vessel. A contrasting member is disposed on at least a portion of the hub assembly, so that when blood enters the chamber, the member provides a high-contrast background when viewed through the window section.

The present invention provides a device that is less complex in structure, manufacture and operation as compared to prior art devices. These and other objects and advantages of the invention will become apparent upon reading the following detailed description and claims, and upon reference to the accompanying drawings.

BRIEF DESCRIPTION OF THE DRAWINGS

For a fuller understanding of the nature and desired objects of the present disclosure, reference is made to the following detailed description taken in conjunction with the accompanying drawing figures wherein like reference characters denote corresponding parts throughout the several views and wherein:

FIG. 1D is an exploded perspective view of the medical device shown in FIG. 1A;

FIG. 3E is a cross-sectional view of the hub assembly shown in FIG. 3C taken along section line 3E-3E of FIG. 3C;

FIG. 3F is a front view of the hub assembly shown in FIG. 3B rotated 90 degrees counterclockwise;

FIG. 3M is a side view of the hub assembly shown in FIG. 3J;

FIG. 3N is a cross-sectional view of the hub assembly shown in FIG. 3M;

FIG. 3O is a back view of the hub assembly shown in FIG. 3A;

FIG. 3P is a perspective view of a needle hub;

DEFINITIONS

Figure 1A:
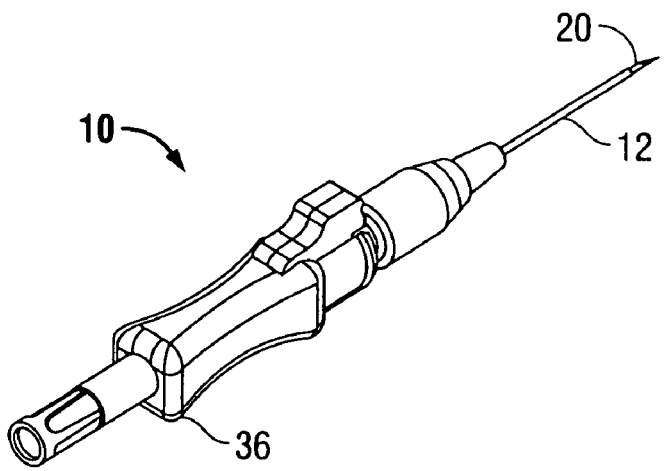
FIG. 1A is a perspective view of a medical device according to an exemplary embodiment of the present disclosure.
Figure 1B:
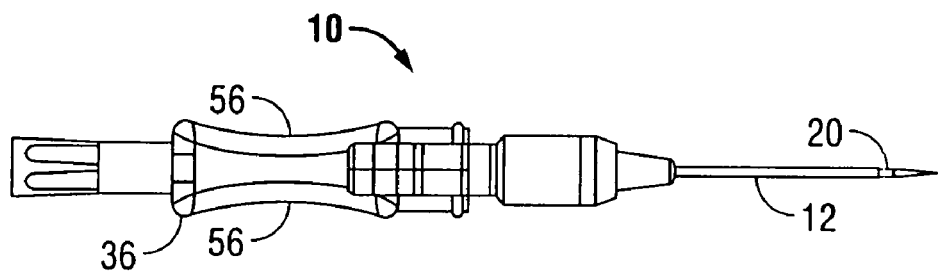
FIG. 1B is a schematic top view of the medical device shown in FIG. 1A.

The following definitions are for convenient reference with respect to the following description and are not to be construed in a limiting manner.

The term "proximal" shall be understood to mean or refer to a location on the device, object or part being discussed which is closest to the medical personnel and farthest from the patient in connection with whom the device is used when the device is used in its normal operation, or a direction toward the medical personnel and away from the patient.

The term "distal" shall be understood to mean or refer to a location on the device, object or part being discussed which is farthest from the medical personnel and closest to the patient in connection with whom the device is used when the device is used in its normal operation, or a direction away from the medical personnel toward the patient.

The term "medical personnel" shall be understood to be generally inclusive of clinicians, surgeons, medical technicians, lab technicians, nurses, nurse practitioners, physician's assistants, veterinarians and veterinary assistants, or other persons who are involved with the use of medical infusion or access devices.

The term "patient" shall be understood to include both humans and animals and also shall be inclusive of humans or animals that are undergoing medical procedures including but not limited to surgical procedures and diagnostic procedures, medical treatment and/or other techniques/procedures/treatments performed in hospitals, clinics, doctor's offices, diagnostic facilities/laboratories or the like, which involve use of medical infusion or access devices.

DETAILED DESCRIPTION

In its broadest aspects, the present disclosure features vascular access devices with enhanced flashback visualization and methods of using such devices. The exemplary embodiments of the device with enhanced flashback visualization and methods of using such devices are discussed in terms of medical access devices such as, for example, infusion devices, over-the-needle catheters, other catheters and feeding tubes used for administration of fluids to patients. It is envisioned, and is thus within the scope of the present invention, for such a device to be adapted for use with a wide variety of medical devices for the infusion of medications and therapeutics to a patient. It is also envisioned that the present invention is used for the collection of body fluids including those collected during procedures relating to phlebotomy, digestive, intestinal, urinary and lumbar puncture. All relative descriptions herein such as top, bottom, left, right, up, and down are with reference to the figures, and thus should not be construed in a limiting sense.

Referring to FIGS. 1A-1E, there is shown a vascular access device 10 with enhanced flashback visualization according to a first exemplary embodiment of the present disclosure. As indicated above, the vascular access device 10 allows medical personnel to more easily visualize blood flashback to ensure proper placement of a catheter in the blood vessel (e.g., vein or artery) of a patient. The vascular access device 10 includes a catheter 12 having a proximal end 14, a distal end 16 and defining a lumen 18. A needle 20 having a proximal end 22 and a distal end 24 is slidably mounted in the lumen 18 of the catheter 12.

Figure 1C:
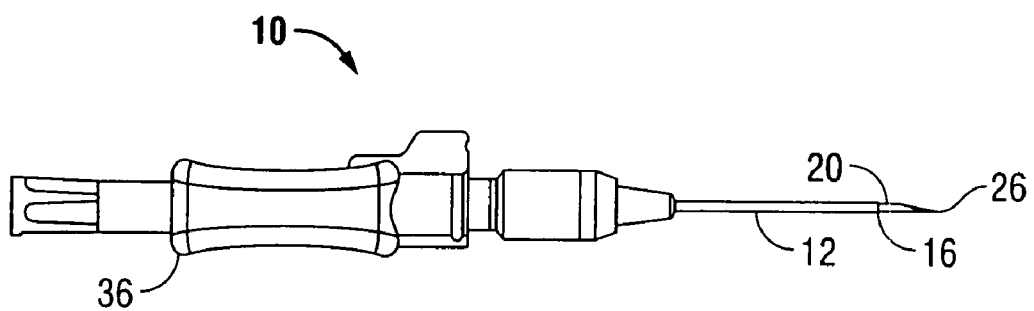
FIG. 1C is a schematic side view of the medical device shown in FIG. 1A.
Figure 1E:
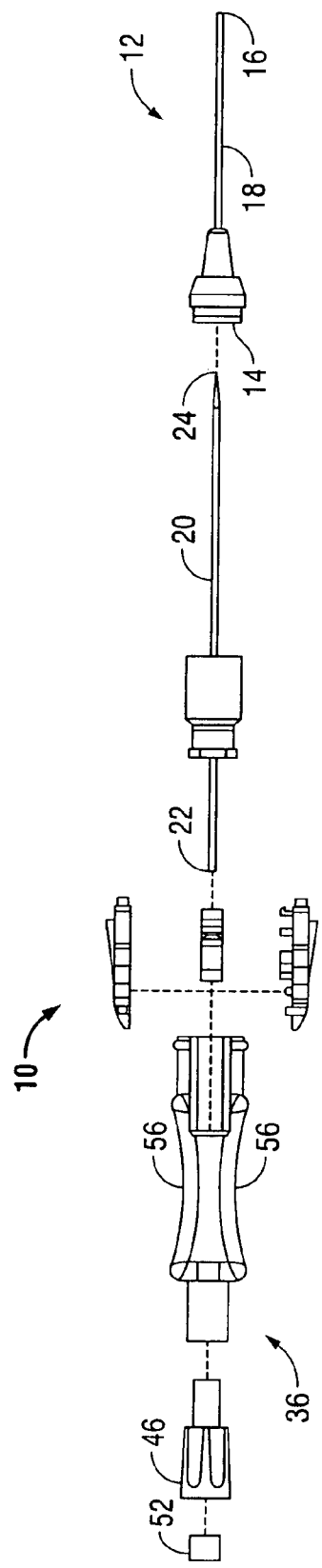
FIG. 1E is an exploded top view of a medical device shown in FIG. 1B.

Referring now to FIGS. 2A-2F, the distal end 24 of the needle 20 is sharpened to a point 26 which protrudes a slight distance past the distal end 16 of the catheter 12 (FIG. 1C). The sharpened point 26 punctures the skin and blood vessel of a patient and allows the distal end 24 of the catheter 12 to be inserted into the patient's blood vessel. The needle 20 includes a lumen 28 extending from a distal opening 30 to a proximal opening 34. The needle 20 also defines a notch opening 32 (FIG. 2E) that is near but spaced apart from the distal opening 30. Upon insertion of the distal end 24 of the needle 20 into the patient's blood vessel, blood flows into the distal opening 30, up through the lumen 28 and then out through the notch opening 32 and the proximal opening 34. The blood exiting the notch opening 32 flows into an annular space (not shown) between the needle 20 and the catheter 12.

This blood exiting into the annular space provides an early indication to the medical personnel that a blood vessel has been punctured.

Figure 2A:
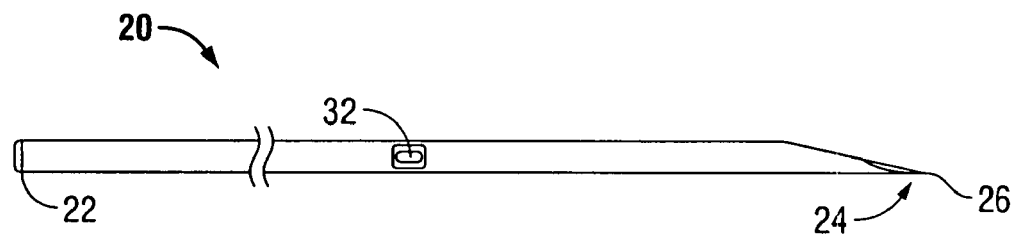
FIG. 2A is a side view of a needle according to an exemplary embodiment of the present disclosure.
Figure 2B:
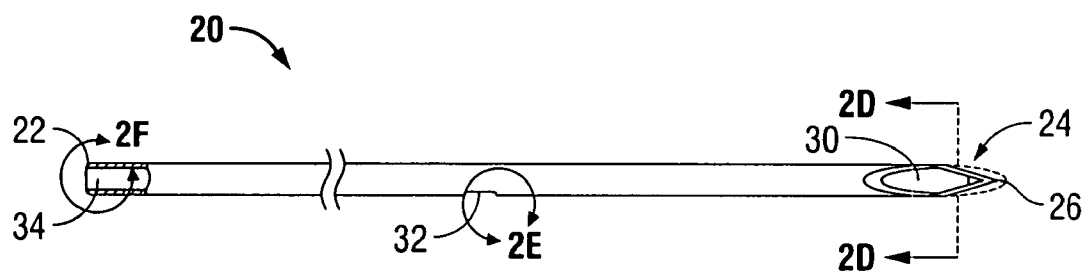
FIG. 2B is a top view of the needle shown in FIG. 2A.
Figure 2C:
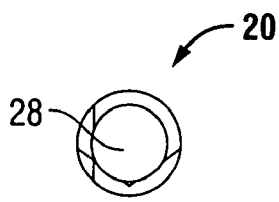
FIG. 2C is a front view of the needle shown in FIG. 2A.
Figure 2D:
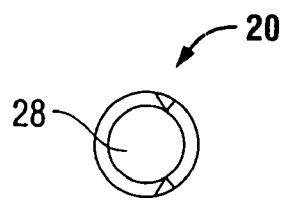
FIG. 2D is a cross-sectional view of the needle shown in FIG. 2B taken along the section line 2D-2D of FIG. 2B.
Figure 2E:
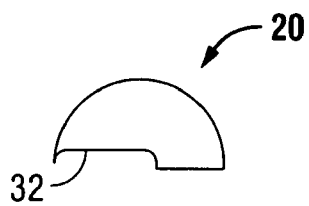
FIG. 2E is an enlargement of area 2E shown in FIG. 2B.
Figure 2F:
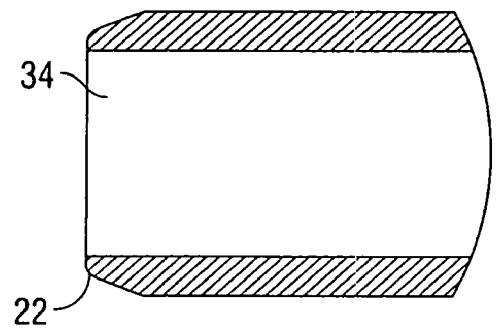
FIG. 2F is an enlargement of area 2F shown in FIG. 2B.
Figure 2G:
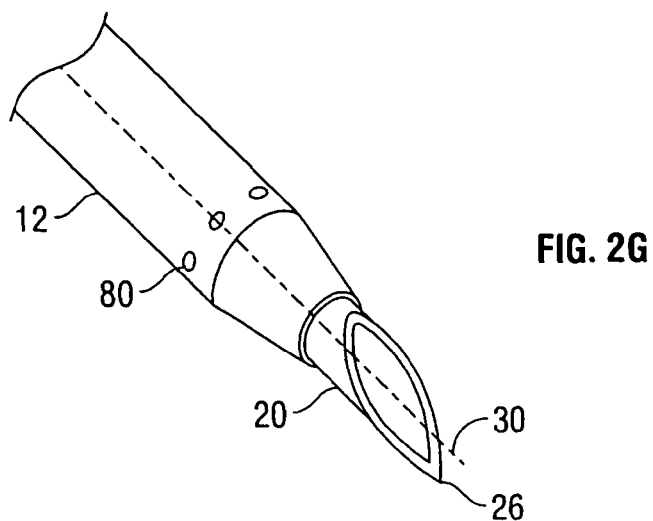
FIG. 2G is an enlarged perspective view of an alternative exemplary embodiment of a needle slidably mounted in a catheter with perforations near the distal end.
Figure 2H:
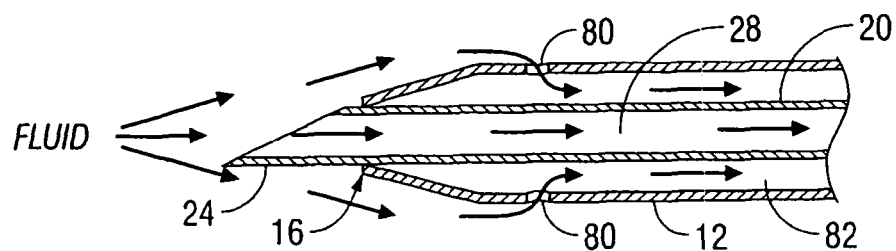
FIG. 2H is a cross sectional view of the enlarged view of FIG. 2G.

Referring now also to FIGS. 2G and 2H, there is shown an alternate exemplary embodiment for providing medical personnel with an early indication that a blood vessel has been punctured. In this exemplary embodiment the distal end 16 of the catheter 12 includes perforations 80 through the catheter 12 wall allowing fluid outside the catheter 12 to be put in fluid communication with the annular space 82 between the needle 20 and the catheter 12. Thus, when the catheter distal end 16 is located within the blood vessel, blood can flow through the perforations 80 into the annular space 82.

Figure 2I:
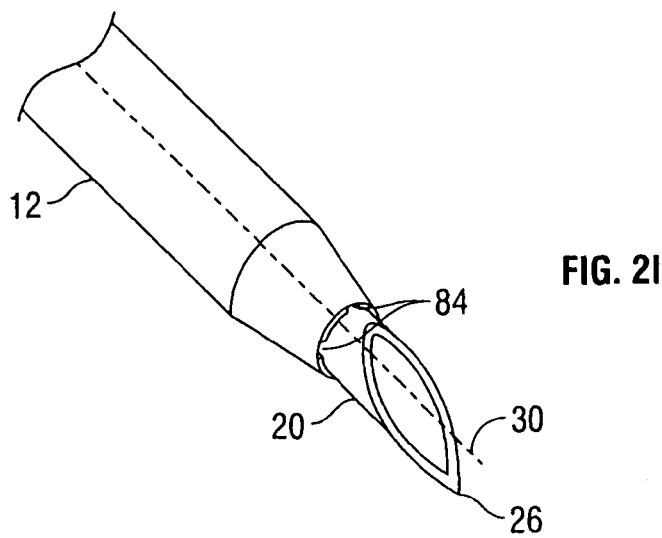
FIG. 2I is an enlarged perspective view of an alternative exemplary embodiment of a needle slidably mounted in a catheter with corrugations along the exterior of the needle and/or the interior of the catheter.
Figure 2J:
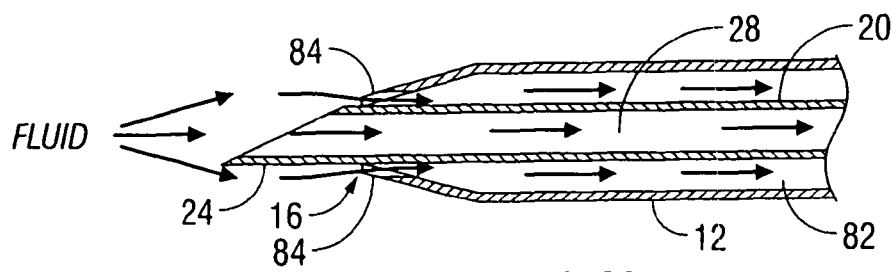
FIG. 2J is a cross sectional view of the enlarged view of FIG. 2I.

Referring now also to FIGS. 2I and 2J, there is shown yet another alternative exemplary embodiment for providing medical personnel with an early indication that a blood vessel has been punctured. In this exemplary embodiment, bumps or corrugations 84 are provided on the exterior surface of the needle 20 and/or the interior surface of the catheter 12 so that a flow path is established between the vessel and the annular space 82, thereby allowing fluid to flow into the annular space 82. It will be apparent to one skilled in the art that other fabrication techniques also would be appropriate to provide an early indication that a blood vessel has been punctured.

It is contemplated that the needle 20 can be any type of needle including, for example, a thoracentesis needle, Veress needle, or Huber needle. It is envisioned that the needle 20 can be fabricated from stainless steel in a range of sizes, including, but not limited to, about 14 to 26 gauge, although smaller or larger sizes can be used depending on the requirements of a particular application. The needle 20 can also be provided in various lengths, for example, about 2.2 to 3.6 inches, although shorter or longer lengths are also envisioned.

Figure 3A:
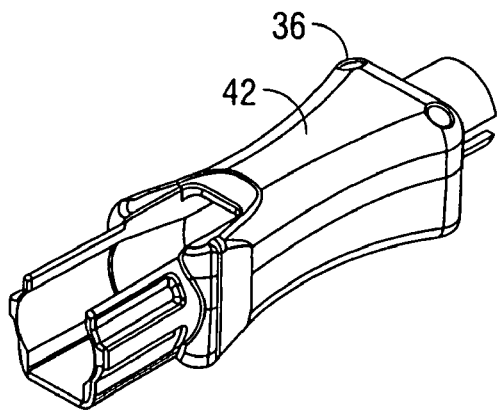
FIG. 3A is a perspective view of a hub assembly according to an exemplary embodiment of the present disclosure.
Figure 3B:
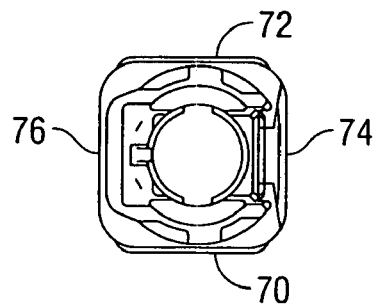
FIG. 3B is a front view of the hub assembly shown in FIG. 3A.
Figure 3C:
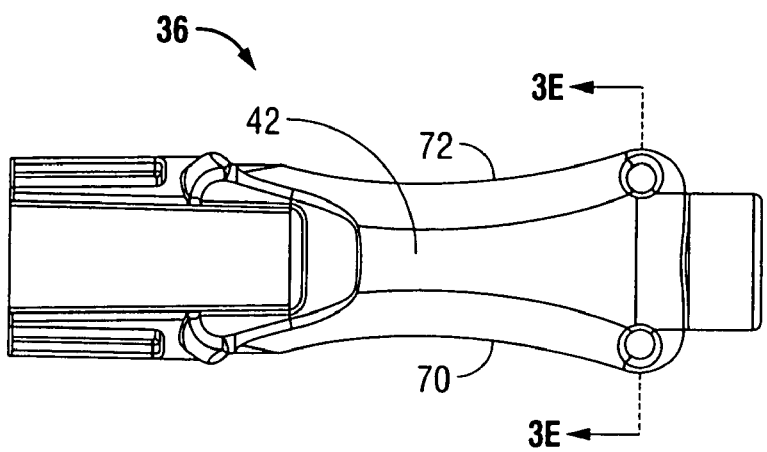
FIG. 3C is a top view of the hub assembly shown in FIG. 3A.
Figure 3D:
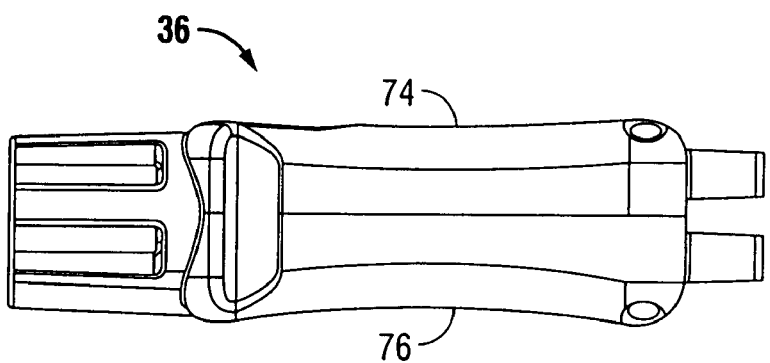
FIG. 3D is a side view of the hub assembly shown in FIG. 3A.
Figure 3G:
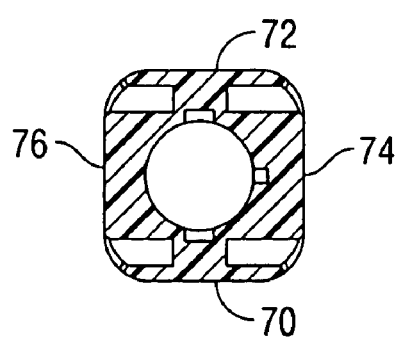
FIG. 3G is a cross-sectional view of the hub assembly shown in FIG. 3F taken along section line 3G-3G of FIG. 3F.
Figure 3G:
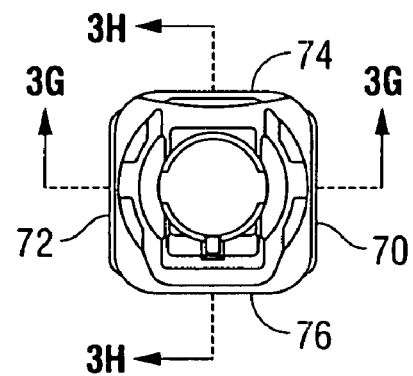
Figure 3G:
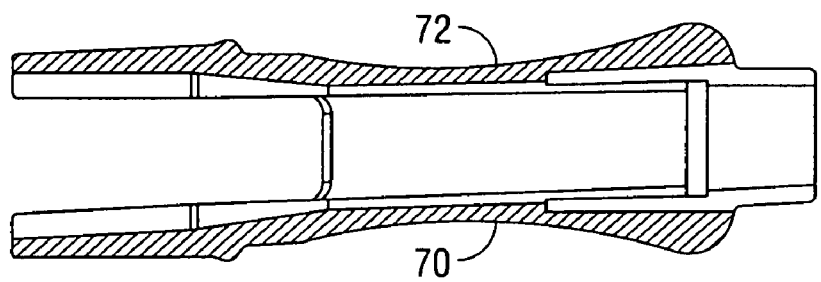
Figure 3H:
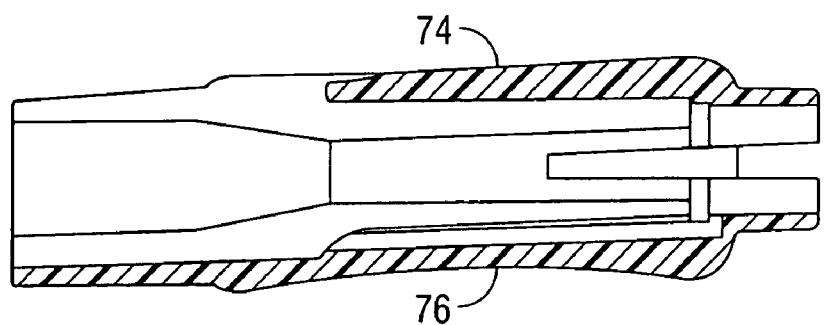
FIG. 3H is a cross-sectional view of the hub assembly shown in FIG. 3F taken along section line 3H-3H of FIG. 3F.
Figure 3I:
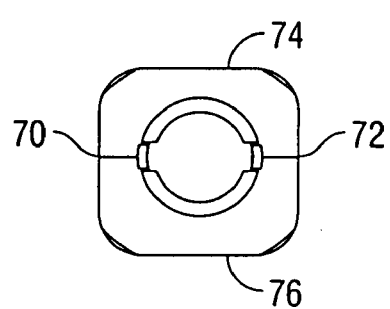
FIG. 3I is a back view of the hub assembly shown in FIG. 3A.
Figure 3J:
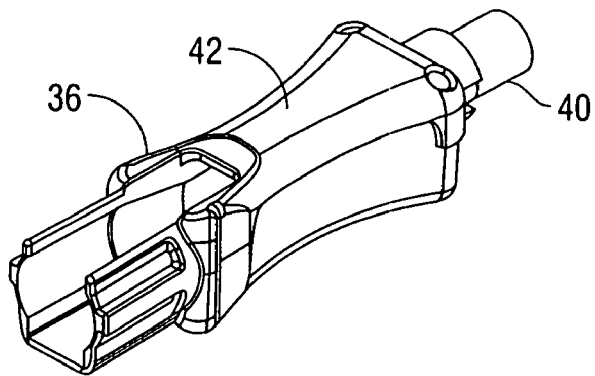
FIG. 3J is a perspective view of the hub assembly shown in FIG. 3A with a needle hub in place.
Figure 3K:
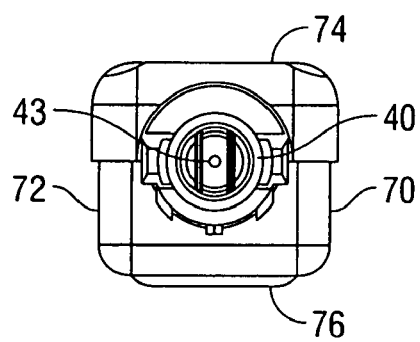
FIG. 3K is a front view of the hub assembly shown FIG. 3J.
Figure 3L:
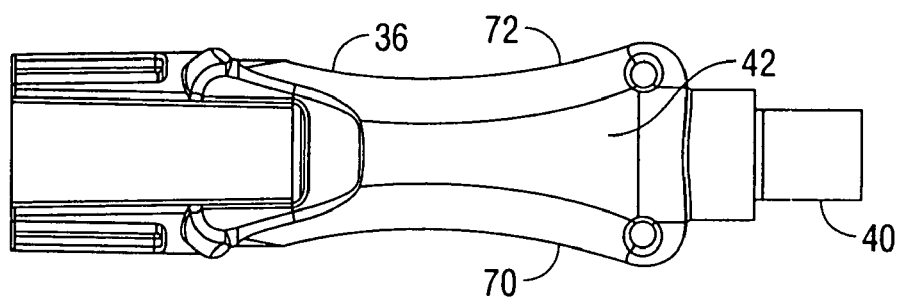
FIG. 3L is a top view of the hub assembly shown in FIG. 3J.
Figure 4A:
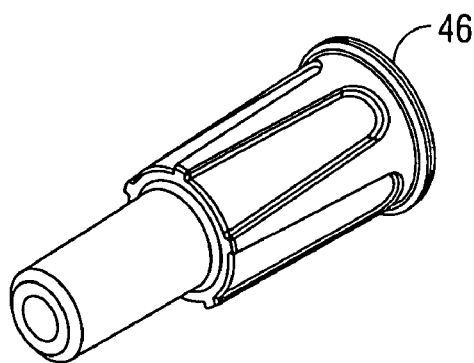
FIG. 4A is a perspective view of a filter housing according to an exemplary embodiment of the present invention.
Figure 4B:
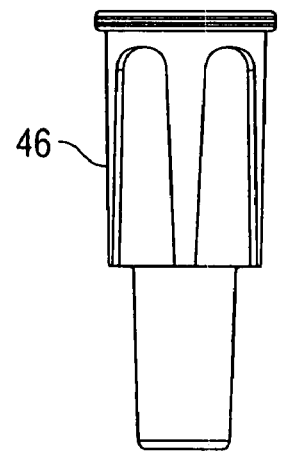
FIG. 4B is a side view of the filter housing shown in FIG. 4A.
Figure 4C:
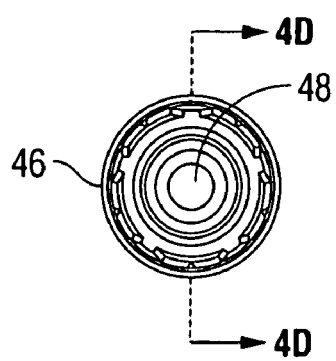
FIG. 4C is a back view of the filter housing shown in FIG. 4A.
Figure 4D:
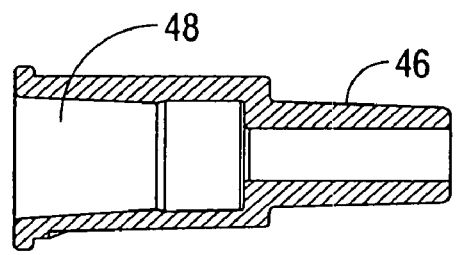
FIG. 4D is a cross-sectional view of the filter housing shown in FIG. 4C taken along section line 4D-4D of FIG. 4C.
Figure 4E:
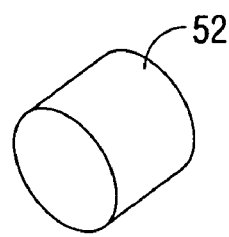
FIG. 4E is a perspective view of filter plug according to an exemplary embodiment of the present disclosure.

The proximal end 22 of the needle 20 is connected to the hub assembly 36 (FIG. 1A). Referring now to FIGS. 3A-3P, the hub assembly 36 is generally rectangular in cross section, having two sides 70, 72, a top 74 and a bottom 76, and includes window section 42. The hub assembly 36 further includes a needle hub 40 (FIG. 3P) adapted to selectively secure the proximal end 22 of the needle 20 to the hub assembly 36. The needle hub 40 includes a cavity or a flashback chamber 38. The needle 20 is received through an inlet 43 in the needle hub 40 and fluidly coupled to the flashback chamber 38 (FIG. 3N). It is envisioned that the proximal end 22 of the needle 20 (FIG. 1D) will protrude about 0.0 to 2.0 millimeters into the flashback chamber 38, although greater protrusion is acceptable. When the medical personnel insert the needle 20 into a blood vessel, the blood flows into the distal opening 30, up through the lumen 28 and then out through the proximal opening 34 into the flashback chamber 38. As a result, the medical personnel can visualize blood entering the flashback chamber 38 through the window section 42 and are provided with a visual indication that the needle 20 is properly positioned in the blood vessel. It is also envisioned that the window section 42 can be convex, or curved in such a way to magnify the blood in the flashback chamber 38.

The hub assembly 36 including the needle hub 40 are fabricated from materials suitable for medical applications, such as, for example, semi-rigid and rigid polymerics as well as resilient materials, such as molded medical grade polypropylene. It is also envisioned that the hub assembly 36 can be fabricated from a transparent (or clear) bio-compatible plastic, so that when blood enters the flashback chamber 38, it can be easily visualized by the medical personnel. One skilled in the art will realize that other materials and fabrication methods also would be appropriate. The hub assembly 36 also can be semi-transparent, translucent or opaque, provided however, window section 42 of the hub assembly 36 is transparent, or substantially transparent so that blood flashback can be easily visualized in the flashback chamber 38.

Referring now to FIG. 4A-4E, the hub assembly 36 (FIG. 1D) further includes a filter housing 46. The filter housing 46 is generally tubular and defines an outlet 48 fluidly coupled to the flashback chamber 38 to allow air to escape therefrom. In an exemplary embodiment, the filter housing 46 includes a filter plug 52 (FIG. 4E) disposed in the outlet 48. The filter plug 52 can be made from a number of materials known in the art which allow air to pass through, but are impermeable or semi-impermeable to liquids such as blood, so that the blood is prevented from leaking out of the flashback chamber 38. As shown, the filter housing 46 is tubular, although other shapes and sizes will be apparent to one skilled in the art depending on the requirements of any particular application. It is envisioned, and thus within the scope of the present disclosure that the entire hub assembly 36 can be fabricated in one piece or in multiple components. The multiple components, for example, a handle, needle hub and filter housing, are then assembled and held together with mechanical fasteners, heat or ultrasonic welding, adhesives, or by other means or techniques known to those skilled in the art. A multiple component hub assembly 36 provides many advantages, including, for example, simpler and more flexible methods of manufacturing various size IV catheters.

The foregoing is illustrative and is not limiting, as it would be apparent to one skilled in the art that any number of structures or devices can be used to create a barrier that is impermeable or semi-impermeable to liquids but which is gas permeable. For example, the filter housing outlet 48 can be capped off and the mechanism capping off the outlet 48 can include a plurality of through apertures that are sized so as to have the above desired gas permeable/liquid impermeable characteristics.

Figure 5A:
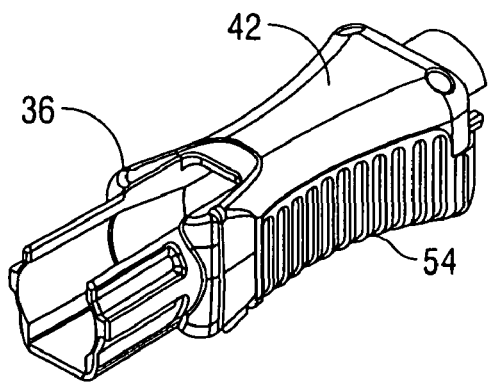
FIG. 5A is a perspective view of a hub assembly according to an exemplary embodiment of the present disclosure.
Figure 5B:
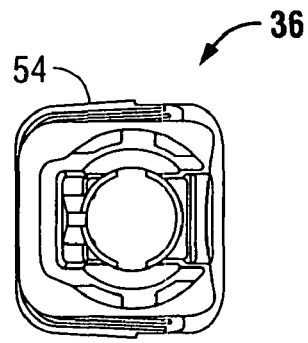
FIG. 5B is a front view of the hub assembly shown in FIG. 5A.
Figure 5C:
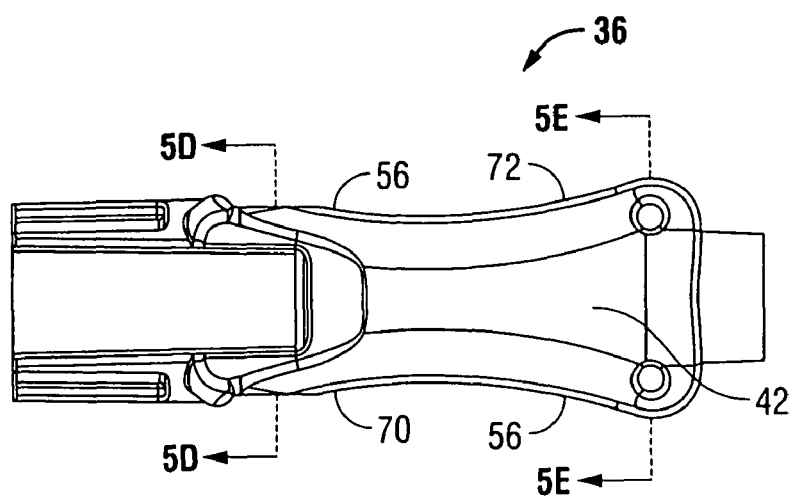
FIG. 5C is a top view of the hub assembly shown in FIG. 5A.
Figure 5D:
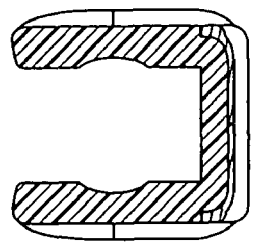
FIG. 5D is a cross-sectional view of the hub assembly shown in FIG. 5C taken along the line B-B.
Figure 5E:
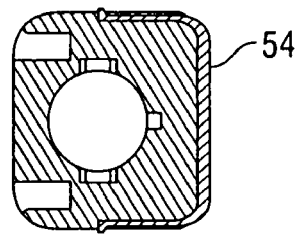
FIG. 5E is a cross-sectional view of the hub assembly shown in FIG. 5C taken along the line A-A.
Figure 5F:
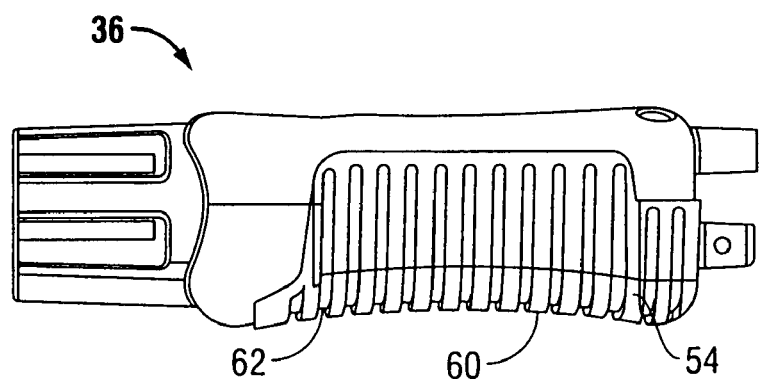
FIG. 5F is a side view of the hub assembly shown in FIG. 5A.
Figure 5G:
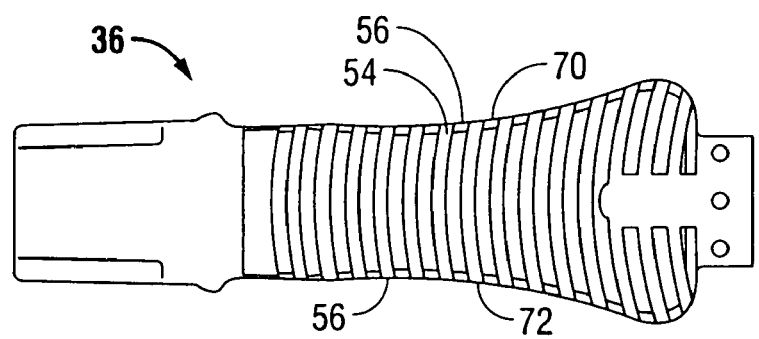
FIG. 5G is a bottom view of the hub assembly shown in FIG. 5A.
Figure 5H:
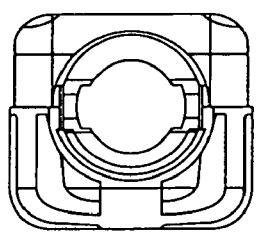
FIG. 5H is a back view of the hub assembly shown in FIG. 5A.
Figure 5I:
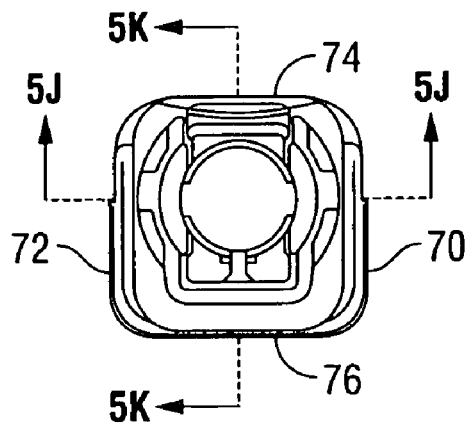
FIG. 5I is a front view of the hub assembly shown in FIG. 5B rotated 90 degrees counterclockwise.
Figure 5J:
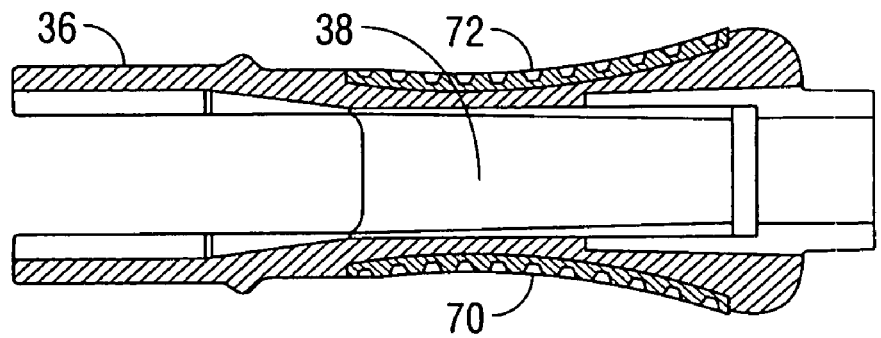
FIG. 5J is a cross-sectional view of the hub assembly shown in FIG. 5I taken along the line E-E.
Figure 5K:
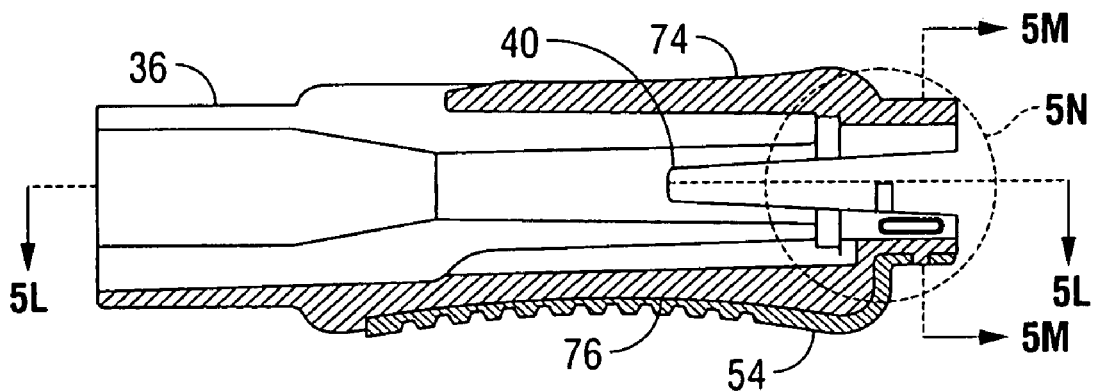
FIG. 5K is a cross-sectional view of the hub assembly shown in FIG. 5I taken along the line F-F.
Figure 5L:
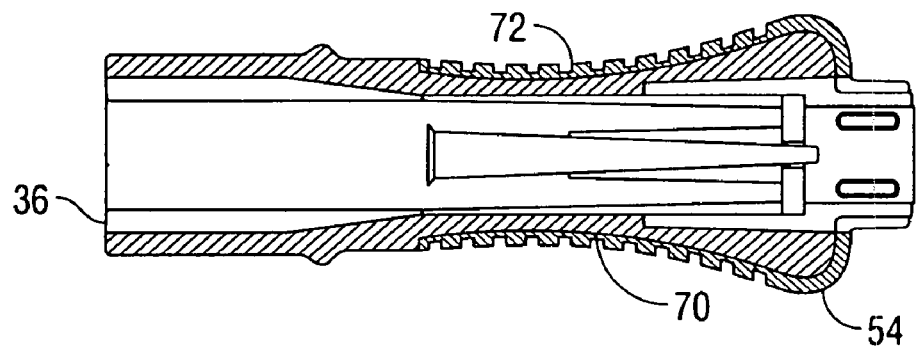
FIG. 5L is a cross-sectional view of the hub assembly shown in FIG. 5K taken along the line G-G.
Figure 5M:
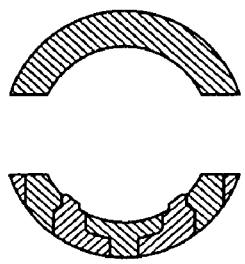
FIG. 5M is a cross-sectional view of the hub assembly shown in FIG. 5K taken along the line H-H.
Figure 5N:
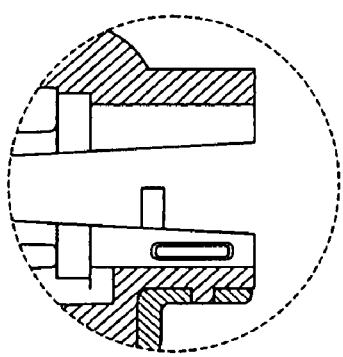
FIG. 5N is an enlarged cross-sectional view of a portion of the hub assembly shown in FIG. 5K.

Referring now to FIGS. 5A-5N, a contrasting member 54 can be disposed on the hub assembly 36 to provide a high-contrast background to enhance detection and visibility of blood or other body fluids in the flashback chamber 38. This contrasting member 54 provides many advantages, including, for example, earlier, easier, and more definitive detection of blood in the flashback chamber 38. Visualization of blood in the flashback chamber provides an indication to the medical personnel that the distal end 24 of the needle 20, and thus the distal end 16 of the catheter 12, has penetrated a blood vessel of the patient. In an illustrative exemplary embodiment, the contrasting member 54 is opaque, white and uniformly disposed on the hub assembly 36. It is envisioned, and thus within the scope of the present disclosure that the color, transparency, reflectance, and coverage of the contrasting member 54 is generally selected so as to provide an effective background for the type of fluid that would appear in the flashback chamber 38.

The hub assembly 36 includes depressed regions or hollows 56 formed on one or both opposing sides 70, 72 to allow for digit placement by the medical personnel. The contrasting member 54 is substantially disposed on both hollows 56, and the bottom 76 of the hub assembly 36. As shown in FIG. 5F, the contrasting member 54 further includes alternating raised portions 60 and indented portions 62 to provide a more secure gripping surface or grip for the medical personnel. In further embodiments, the contrasting member 54 can be disposed on any portion of the hub assembly 36. Additional examples and patterns of contrasting members 54 will be apparent to one skilled in the art.

In one embodiment, the contrasting member 54 is disposed on at least a portion of the hub assembly 36 opposite the medical personnel's line of sight, such that when viewing through the window section 42, the contrasting member 54 provides the desired contrast at a variety of viewing angles. In the illustrated embodiment, the medical personnel would place their thumb and finger in the hollows 56 of the hub assembly 36 when inserting the medical device into a patient. The medical personnel may then visualize the flashback chamber 38 through the window section 42 of the hub assembly 36.

In particular embodiments, the contrasting member 54 is an integral part of the hub assembly 36, or is secured/applied to the surface(s) thereof. Numerous materials and fabrication techniques will be apparent to one skilled in the art including, for example, molding, injection molding, two-shot molding, over-molding, printing, painting and adhesive labeling. It is envisioned, and is thus within the scope of the present disclosure, for such fabrication techniques to include processes whereby the molded material has a translucent or opaque region sufficient to provide a high contrast background. It is also envisioned that the contrasting member 54 is a separate component part (e.g., a molded part) that is then secured to the hub assembly 36. It will be apparent to one skilled in the art that a separate contrasting member 54 can be secured to the hub assembly 36 in any of a number of ways including, for example, snap on, mechanically fastened, heat welding, vibration welding, ultrasonically welding, or boding with an adhesive.

It is also envisioned that one or more surfaces of the hub assembly 36 and/or needle hub 40 can be treated or processed (e.g., chemically etched, sand blasted, etc.) so as to provide a surface finish that creates a contrasting surface. In further embodiment, such a surface finish or treatment is achieved by use of an appropriate manufacturing technique (e.g., molding the part using a mold including a textured surface so that the part is formed with a textured translucent surface).

In alternative embodiments, the contrasting member can be intermittently disposed on the hub assembly 36 (e.g., the contrasting member could be formed with raised sections 60 but without the interconnecting indent sections 62). The intermittent sections of contrasting member can be raised from the surface of the hub assembly 36 to provide a more secure grip for the medical personnel. Medical personnel sometimes place their thumb or finger on the top 74 and the bottom 76 of the hub assembly 36 when inserting the medical device 10 into a patient. In this alternative embodiment, the intermittent sections of contrasting member allows the medical personnel to visualize blood entering the flashback chamber 38 through the alternating transparent regions of the hub assembly 36 and opaque regions of the contrasting member.

In operation, the medical personnel grips the vascular access device 10 by placing a thumb and finger in the hollows 56 of the hub assembly 36 and inserts the sharpened point 26 of the needle 20 into the blood vessel of a patient. Once the distal end 24 of the needle 20 punctures a blood vessel, blood will begin to flow in to the lumen 28 at least through capillary action and/or due to vascular pressure. Blood will first flow through the notch opening 32, perforations 80, or corrugations 84 into the annular space 82 between the needle 20 and the catheter 12, providing an early indication to the medical personnel that a blood vessel has been punctured. As the distal end 24 of the needle 20 and the distal end 16 of the catheter 12 are further inserted into the proper location of the blood vessel, vascular blood pressure pushes blood up through the lumen of the needle and eventually out of the proximal end 22 of the needle 20 into the flashback chamber 38. The air in the flashback chamber 38 also passes through the filter plug 52, for example to facilitate the flow of blood into the flashback chamber. As the filter plug 52 is impermeable to liquids such as blood, the blood is prevented from leaking out of the flashback chamber 38.

As blood enters the flashback chamber 38, the medical personnel visualize the blood through the window 42 and against the contrasting member 54 instead of other backgrounds such as, for example, the skin of the patient as in conventional devices which can be dark with minimal contrast if the patient is bruised or has a dark complexion. Additionally, visualization of blood may be provided by viewing through the proximal region of the needle hub 40 (FIG. 3P), which extends proximally beyond the window section 42. Consequently, the medical personnel are provided with visual indication that the catheter 12 is properly positioned in the blood vessel.

Although the embodiments of the disclosure have been described using specific terms, such description is for illustrative purposes only, and it is to be understood that changes and variations may be made without departing from the spirit or scope of the following claims.

INCORPORATION BY REFERENCE

The entire contents of all patents, published patent applications and other references cited herein are hereby expressly incorporated herein in their entireties by reference.

What is claimed is:

1. A medical infusion device for vascular access with enhanced flashback visualization, comprising:
a hub assembly having a proximal portion, a distal portion, a substantially transparent window section, the window section being disposed between the proximal portion and the distal portion;
a needle hub mounted on the hub assembly, the needle hub defining a flashback chamber therein, wherein the flashback chamber is received within the hub assembly;
a needle having a proximal end, a distal end and a lumen therethrough, the lumen being fluidly coupled to the flashback chamber to allow fluid to flow through the lumen into the flashback chamber; and
a contrasting member disposed on at least a portion of an outer surface of the hub assembly, the contrasting member being a patterned member and having a color that provides an effective background to fluid in the flashback chamber, the contrasting member including a portion opposite from the window section such that fluid in the flashback chamber can be viewed through the substantially transparent window section against the contrasting member.

2. The medical infusion device of claim 1, wherein the hub assembly is substantially transparent.

3. The medical infusion device of claim 1, wherein the hub assembly further includes an outlet fluidly coupled to the flashback chamber and the outlet is configured so as to be gas-permeable and substantially impermeable to liquid.

4. The medical infusion device of claim 3, wherein the outlet includes a gas-permeable member disposed therein.

5. The medical infusion device of claim 1, wherein the hub assembly includes depressed hollows formed on at least one opposing side of the hub assembly.

6. The medical infusion device of claim 1, wherein the contrasting member includes alternating raised portions and indented portions.

7. The medical infusion device of claim 1, wherein the contrasting member is a coating applied to the hub assembly.

8. The medical infusion device of claim 1, wherein the contrasting member is formed by a molding process.

9. The medical infusion device of claim 8, wherein the molding process is two-shot injection molding.

10. The medical infusion device of claim 8, wherein the molding process is over-molding.

11. The medical infusion device of claim 1, wherein the needle hub extends proximally beyond the window section such that a proximal portion of the needle hub provides visual indication of fluid therein.

12. A medical infusion device with enhanced flashback visualization, comprising:
- a hub assembly including a proximal portion, a distal portion, and a substantially transparent window section intermediate the proximal portion and distal portion;
- wherein the hub assembly includes an outlet and a plug in the outlet to allow egress of gas therethrough;
- a needle hub mounted on the hub assembly, the needle hub defining a chamber therein, wherein the chamber is received within the huh assembly;
- a needle including a lumen fluidly coupled to the chamber so that fluid can flow through the lumen into the chamber; and
- a contrasting member disposed on at least a portion of an outer surface of the hub assembly, the contrastive member having a color that provides an effective background to fluid in the chamber, the contrasting member including a portion opposite from the window section such that fluid in the chamber is viewed through the window against the contrasting member, the contrasting member including alternating raised portions and indented portions;
- wherein the contrasting member is formed by a two-shot injection molding process.

13. A medical infusion device with enhanced flashback visualization, comprising;
- a hub assembly including a proximal portion, a distal portion, and a substantially transparent window section intermediate the proximal portion and distal portion;
- wherein the hub assembly includes an outlet and a plug in the outlet to allow egress of gas therethrough;
- a needle hub mounted on the hub assembly, the needle hub defining a chamber therein, wherein the chamber is received within the hub assembly;
- a needle having a lumen fluidly coupled to the chamber so that fluid can flow through the lumen into the chamber; and
- a contrasting member disposed on at least a portion of an outer surface of the hub assembly, the contrasting member having a color that provides an effective background to fluid in the chamber, and the contrasting member including raised sections intermittently disposed on at least a portion of the hub assembly, the contrasting member including a portion opposite from the window section such that fluid in the chamber is viewed through the window against the contrasting member.

14. The medical infusion devise of claim 13, wherein the hub assembly includes hollows formed on at least two opposing sides allowing for improved grip by a user.

15. The medical infusion device of claim 14, wherein the contrasting member is disposed in the hollows and is formed by a two-shot injection molding process.

16. The medical infusion device of claim 1, wherein the window section exhibits an arcuate configuration.

17. The medical infusion device of claim 16, wherein the arcuate configuration exhibited by the window section is convex.

18. The medical infusion device of claim 1, wherein the contrasting member is snapped onto the hub assembly.

19. The medical infusion device of claim 1, wherein the contrasting member is opaque and white.

* * * * *